(12) United States Patent
Fox Linton et al.

(10) Patent No.: US 6,216,094 B1
(45) Date of Patent: Apr. 10, 2001

(54) METHOD OF AND APPARATUS FOR ANALYZING A SIGNAL

(75) Inventors: Robert Anthony Fox Linton, London; David Marston Band, Surbiton; Nicholas William Fox Linton, London, all of (GB)

(73) Assignee: Monitoring Technology Limited, London (GB)

( * ) Notice: Subject to any disclaimer, the term of this patent is extended or adjusted under 35 U.S.C. 154(b) by 0 days.

(21) Appl. No.: 08/894,571

(22) PCT Filed: Feb. 22, 1996

(86) PCT No.: PCT/GB96/00402

§ 371 Date: Feb. 13, 1998

§ 102(e) Date: Feb. 13, 1998

(87) PCT Pub. No.: WO96/26497

PCT Pub. Date: Aug. 29, 1996

(30) Foreign Application Priority Data

Feb. 24, 1995 (GB) .................................... 9503787

(51) Int. Cl.[7] ....................................... A61B 5/00
(52) U.S. Cl. ................... 702/100; 702/131; 600/481; 600/505; 600/526; 128/898
(58) Field of Search ............... 702/100, 65, 131; 600/481, 505, 526, 549; 128/898

(56) References Cited

U.S. PATENT DOCUMENTS 5,109,862 * 5/1992 George ............................... 600/515
5,425,375 * 6/1995 Donald ................................. 600/549

FOREIGN PATENT DOCUMENTS 0 182 363   5/1986   (EP) .
0 599 314   6/1994   (EP) .

OTHER PUBLICATIONS

"Computerized Analysis of Doppler Transmitral Flow Velocity", Proceedingds of the Computers in Cardiology Meeting, Sep. 12–15, 1987, Leuven, Belgium, by G D'Ambrosio MD et al., pp. 445–448.

"Improved Color Flow Mapping Using the Wideband Maximum Likelihood Estimator", Proceedings of the Ultrasonics Symposium, Dec. 4–7, 1990, Honolulu, Hawaii, by K.W. Ferrara et al., pp. 1517–1521.

* cited by examiner

*Primary Examiner*—Kamini Shah
(74) *Attorney, Agent, or Firm*—Westerman, Champlin & Kelly, P.A.

(57) ABSTRACT

A method of analyzing a signal representing a physical parameter to obtain information from said signal and to extrapolate information contained in said signal and/or to ignore an interfering component in part of said signal, said signal representing either only a first portion of a skew distribution, or a first portion of a skew distribution and a second portion containing an interfering component, in which the area of a skew distribution, preferably a lognormal distribution is measured. The method is particularly applicable to the measurement of cardiac output. Apparatus for carrying out the method is also disclosed.

38 Claims, 4 Drawing Sheets

METHOD OF AND APPARATUS FOR ANALYZING A SIGNAL

BACKGROUND OF THE INVENTION

The present invention relates generally to a method of and apparatus for analyzing a signal representing a physical parameter to obtain information from the signal and to extrapolate information contained in this signal and/or to ignore an interfering component in part of the signal. In particular, the present invention relates to the analysis of a signal representing either only a first portion of a skew distribution, or a first portion of a skew distribution and a second portion containing the interfering component. Particularly, the present invention provides for a method of determining the flow rate of a fluid using a signal analysis technique.

In order to measure flow rate of a fluid theoretically the simplest method is to add an indicator substance at a known concentration and constant rate into the flow and to measure its concentration downstream. Provided perfect mixing has occurred, the dilution factor gives a ratio of the two flows in the steady state. This approach has been used to measure cardiac output.

A more practical method, which has been employed to measure cardiac output, is to add the indicator as a bolus and to measure the concentration time profile of the passage of this bolus at a point downstream. Typically the concentration rises to a rounded peak and falls away more slowly as the remaining indicator is washed out. Such a curve may be considered as a large number of elements of sufficiently short time duration that for each element the flow and concentration are effectively constant. The concentration of the indicator multiplied by the flow and the time duration of each element gives the quantity of marker passed by that element. The sum of these quantities should therefore equal the total quantity of indicator added as the bolus. If the flow is constant for the duration of the curve, i.e. is the same for each of the elements, it may be calculated simply as the quantity of indicator added to the flow, e.g. by injection for cardiac output measurement, divided by the total area under the curve. The shape of the curve is unimportant providing that the total area can be found.

The bolus injection method of measuring cardiac output has been identified as suffering from the problem of the indicator starting to recirculate before the first pass of the indicator has been completed. Because of this recirculation some method is required to estimate the area of the primary curve, i.e. the curve which would have appeared had there been no recirculation, and so the shape of the curve becomes important. In a paper "Studies on the Circulation IV Further Analysis of the Injection Method, and of changes in Hemodynamics under Physiological and Pathological Conditions" by Hamilton et al, American Journal of Physiology 1932, Vol. 99, Pages 534–551, it has been proposed that the down-limb of the curve would, in the absence of recirculation, be monoexponential. The curve was plotted semilogarithmically so that the straight line of the down-limb could be extrapolated to a low value of the indicator concentration. The area which would have been inscribed by the curve representing the first pass of the indicator could therefore be measured. The theoretical basis for this technique has been challenged and a major problem for the use of such a technique clinically is that when the cardiac output is low the degree of encroachment of recirculation (the secondary curve) on the primary curve increases so that the extrapolation becomes unreliable.

The present inventors have developed a technique for analyzing signals which exhibit a skew distribution which avoids the need to measure these signals over the complete distribution or to utilize the part of the skew distribution where there is interference from an extraneous component, e.g. recirculation in the clinical indicator dilution curve technique. This technique can be applied to the analysis of any signals which exhibit a skew distribution and for which the integral of the distribution is required. This technique is however particularly applicable to the clinical indicator dilution technique in order to overcome the problem of recirculation. Such an indicator dilution technique can utilize lithium as the indicator and the invention is therefore particularly suited for the analysis of the indicator dilution curve provided from the cation detector disclosed in WO93/09427.

Although the possibility of modelling indicator dilution curves as a lognormal distribution which is a particular skew distribution has been disclosed in a paper entitled "An Empirical Formula for Indicator Dilution Curves as obtained in Human Beings" by Stow et al (Journal of Applied Physiology (1954), Vol. 7, Pages 161–167), the proposed use of the lognormal distribution to describe the primary curve merely represented the fitting of a mathematical relationship to the data with no theoretical support of the use of such a distribution to describe the indicator dilution curve. This paper further does not disclose how to obtain the area under the curve without being able to some how or other measure the primary curve without compensating for the secondary curve caused by recirculation.

The present inventors have therefore investigated the lognormal distribution in particular for indicator dilution curves to determine whether the lognormal distribution is a useful approximation.

A variable has a lognormal distribution if the logarithm of the variable is normally distributed (Skew Distributions. in Statistical Theory with Engineering Applications. 1952 by D. Hald, published by John Wiley & Sons, New York, London, Pages 159–187).

The equation of the lognormal distribution is $$y = \frac{1}{\sqrt{2\pi}\sigma x} \cdot e^{-(\ln(x)-\mu)^2 + 2\sigma^2}$$

where $\mu$ and $\sigma$ are the mean and standard deviation respectively of the normal distribution from which the logarithmic transformation was obtained. FIG. 1 shows lognormal curves varying from $\sigma=0.1$ to $1.0$, with the values of $\sigma$ indicated above each curve. Skewness is a monotonically increasing function of $\sigma$, so the curves become more skewed as $\sigma$ increases.

To determine whether the lognormal distribution is a good approximation for indicator dilution curves, the modelling of the effect of mixing an indicator of lithium into plasma at a concentration of 6 mM for one second was modelled passing through a cascade of six identical single pole filters each with a time constant of 1.3 seconds. The model used difference equations and the curves after each filter stage can be seen in FIG. 2. With three filter elements the curve is very close to a lognormal distribution and FIG. 3 illustrates an iterative best fit of a lognormal distribution to the third curve of FIG. 2 after the initial signal had passed through three filter elements. For the curve shown in FIG. 3 $\mu=1.76$ and $\sigma=0.347$.

It has also been determined by the inventors that over a range of skewness which is typically encountered in indicator dilution curves the lognormal distribution is a good approximation of the chi squared distribution. FIG. 4 illustrates the relationship between a chi squared distribution for 8 degrees of freedom (equivalent to four filter elements) and a lognormal curve where $\sigma=0.38$ and $\mu=2.32$. The curve represents the lognormal curve and the points represent points from the chi squared distribution. It can be seen from this that there is close approximation.

This work has provided theoretical justification for the use of the lognormal distribution in the analysis of indicator dilution curves and has led the inventors of the present application to develop an accurate and simple method of using the lognormal distribution to analyze indicator dilution curves.

Using the indicator dilution technique the cardiac output can be obtained from the equation $$\frac{\text{cardiac output}}{\text{in l/min}} = \frac{\text{Indicator dose} \times 60}{\text{Total area} \times (1 - \text{PCV})}$$

where PCV is packed cell volume and may be calculated as haemoglobin concentration (g/dl)/33; this correction is needed because the lithium indicator is distributed in the plasma.

In order to calculate the cardiac output it is therefore necessary to determine the total area under the curve. One possible method is an iterative process to fit a lognormal curve to the data points. The use of the lognormal distribution to fit the indicator curve does however allow curves to be analyzed when encroachment of the secondary curve precludes the extrapolation technique used by Hamilton. The drawback of iteration is that it is relatively slow and occasionally unreliable.

The present inventors have therefore developed a technique which measures the area of a skew distribution (particularly the lognormal distribution) in order to overcome the disadvantages in the prior art. Although this technique is particularly applicable to indicator dilution curves in order to determine cardiac output, the technique is generally applicable to the analysis of any signal representing any physical parameter where the signal exhibits a skew distribution.

SUMMARY OF THE INVENTION

In accordance with one aspect the present invention provides a method of analyzing a signal representing a physical parameter to obtain information from said signal and to extrapolate information contained in said signal and/or to ignore an interfering component in part of said signal, said signal representing either only a first portion of a skew distribution, or a first portion of a skew distribution and a second portion containing said interfering component. The method comprises the steps of:

a) selecting two fractions of the maximum value of said signal in said first portion and selecting whether said fractions are to represent positions on said skew distribution having a positive or negative slope, said fractions being used to delineate between first and second parts of said skew distribution, said first and second parts being delineated to lie within said first portion of said skew distribution, b) determining the integrals of said first and second parts, and c) determining the integral of said complete skew distribution using said determined integrals of said first and second parts and a predetermined relationship between the integral of a complete skew distribution and integrals of said first and second parts for said selected fractions.

In accordance with a second aspect the present invention provides apparatus for analyzing a signal representing a physical parameter to obtain information from said signal and to extrapolate information contained in said signal and/or to ignore an interfering component in part of said signal, said signal representing either only a first portion of a skew distribution or a first portion of a skew distribution and a second portion containing said interfering component, said system comprising:

a) means for selecting two fractions of the maximum value of said signal in said first portion and selecting whether said fractions are to represent positions on said skew distribution having a positive or a negative slope, said fractions to be used to delineate between first and second parts of said skew distribution, said first and second parts being delineated to lie within said first portion of said skew distribution, b) means for determining the integrals of said first and second parts, and c) means for determining the integral of said complete skew distribution using said determined integrals of said first and second parts and a predetermined relationship between the integral of a complete skew distribution and integrals of said first and second parts for said selected fractions.

In accordance with a third aspect the present invention also provides a method of determining the flow rate of a fluid, comprising the steps of:

a) adding a known quantity of a substance to said fluid at a point in time, b) measuring the quantity of said substance in said fluid at a point downstream to generate a distribution with respect to time, said distribution approximating either only a first portion of a skew distribution, or a first portion of a skew distribution and a second portion containing extraneous components, c) assuming said distribution can be approximated by a skew distribution and selecting two fractions of the maximum value of said signal in said first portion and selecting whether said fractions are to represent positions on said skew distribution having a positive or a negative slope, said fractions being used to delineate between first and second parts of said skew distribution, said first and second parts being delineated to lie within said first portion of said skew distribution, d) calculating the integrals of said first and second parts, e) determining the integral of the complete skew distribution using said calculated integrals of said first and second parts and a predetermined relationship between integrals of said first and second parts and the integral of said complete skew distribution for said selected fractions, and f) calculating the flow rate of said fluid from said known quantity of said substance and said integral of said complete skew distribution.

In accordance with a further aspect the present invention provides apparatus for determining the flow rate of a fluid comprising:

a) sensor means for measuring the quantity of a substance in said fluid at a point downstream of where a known quantity said substance has been added to said fluid, the measurement generating a distribution with respect to time which approximates either only a first portion of a skew distribution, or a first portion of a skew distribution and a second portion containing extraneous components, b) means for selecting whether two fractions of the maximum value of said signal in said first portion and selecting whether said fractions are to represent positions on said skew distribution having a positive or a negative slope, said fractions to be used to delineate between first and second parts of said skew distribution, said first and second parts being delineated to lie within said first portion of said skew distribution, c) means for calculating the integrals of said first and second parts, d) means for determining the integral of the complete skew distribution using said calculated integrals of said first and second parts and a predetermined relationship between integrals of said first and second parts and the integral of said complete skew distribution for said selected fractions, and e) means for calculating the flow rate of said fluid from said known quantity of said substance and said integral of said complete skew distribution.

Although the present invention is applicable to a signal which forms said first portion only having a positive slope, i.e. the portion of the skew distribution before the peak, preferably said first portion includes the peaks of the skew distribution and said first part generally includes the part of the distribution up to or including the peak, and said second part includes the part of the distribution after the peak (and possibly including the peak). By including the peak in the integrals the integral of the complete skew distribution can be calculated more accurately.

Preferably the skew distribution is a chi squared distribution which can be approximated as a lognormal distribution.

By measuring the areas of a first and second parts of the skew distribution, the necessity to measure the complete skew distribution is avoided. The integral of the complete skew distribution can be calculated merely from making an assumption that the signal represents a portion of the skew distribution and by measuring two areas under the curve. This technique has the advantage that where the signal varies with time, the measurement time is reduced and the problem of interfering components, e.g. recirculation, can be avoided by selection of appropriate fractions of the height of the peak to avoid using the tail of the distribution affected by such interfering components.

Another advantage of the present invention is that since the signal is treated as having a skew distribution, it can be filtered (or integrated) to remove noise. The filter neither alters the area nor affects the skew distribution characteristics (although the mean and standard deviations $\mu$ and $\sigma$ may be affected). The filter produces a smoother curve and therefore allows for the more accurate delineation of the first and second parts of the skew distribution. For indicator curve analysis an approximate time constant of 2.5 seconds provides adequate smoothing without excessively reducing the separation of the primary and secondary curves.

Thus the present invention can be applied to the analysis of any signal representing a physical parameter. For instance the signal can represent the concentration of a substance in a flowing fluid and the calculated integral of the complete skew distribution can be used to calculate the flow rate of the fluid. In an electrical application of the present invention the signal could represent current and the calculated integral of the skew distribution could represent a quantum of charge. The technique of the present invention can therefore be applied to determine the charge resulting from the application of a single pulse of current after the pulse of current has been affected by time constants in a circuit in a like manner to that described with regard to FIG. 2.

In the present invention the predetermined relationship between the integral of a complete skew distribution and integrals of the first and second parts for the selected fractions are used to determine the integral of the complete skew distribution. This relationship can be predetermined by equating the integral of the complete skew distribution divided by the sum of the integral of the first part and the integral of the second part with a function of the ratio of the integral of said first part to the integral of said second part. This relationship can either be used to form a look-up table or it can be used to calculate the integral of the complete skew distribution.

DESCRIPTION OF THE ILLUSTRATIVE EMBODIMENTS

For the lognormal curve in accordance with one embodiment of the present invention, in order to determine the integral of the complete lognormal curve it is necessary to define two areas in a first portion of the curve which is unaffected by recirculation.

Figure 1:
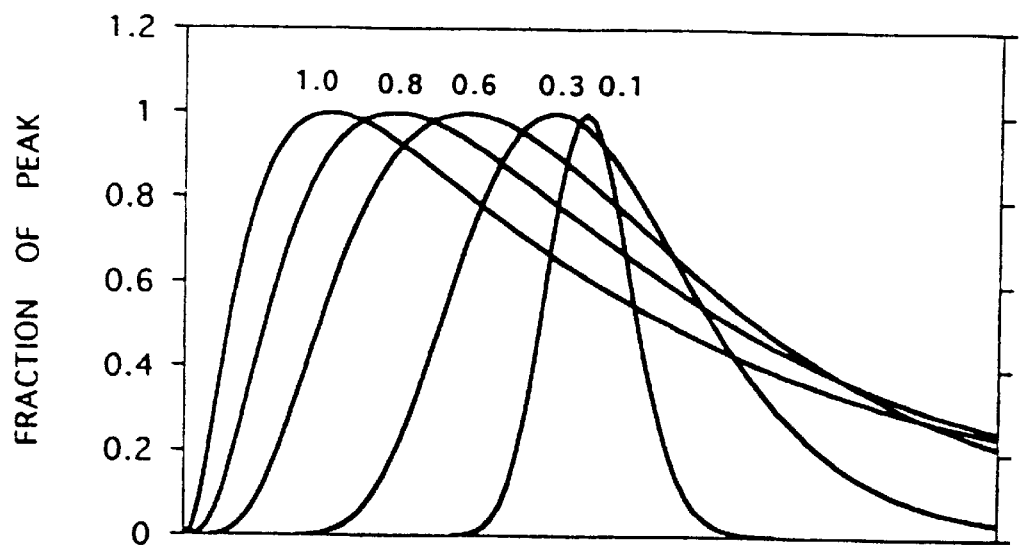
FIG. 1 illustrates lognormal curves for different values of $\sigma$.
Figure 2:
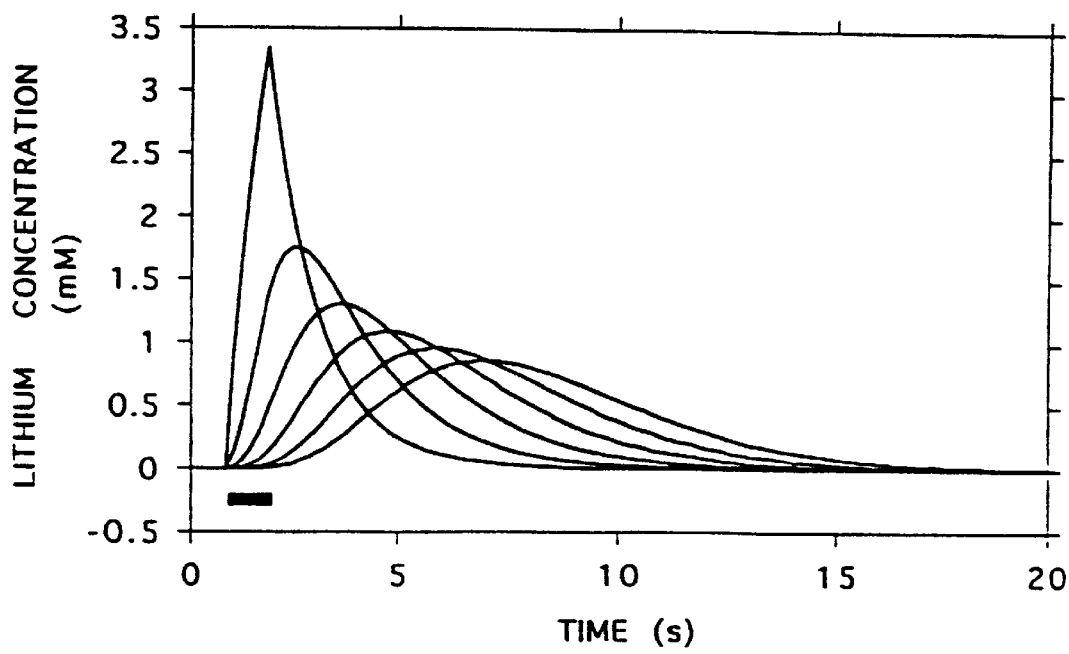
FIG. 2 are curves for lithium concentration being passed through a model of six filters in series each with a time constant of 1.3 seconds. The initial signal was modelled as a plasma lithium concentration of 6 mM for the time indicated by the horizontal bar.
Figure 3:
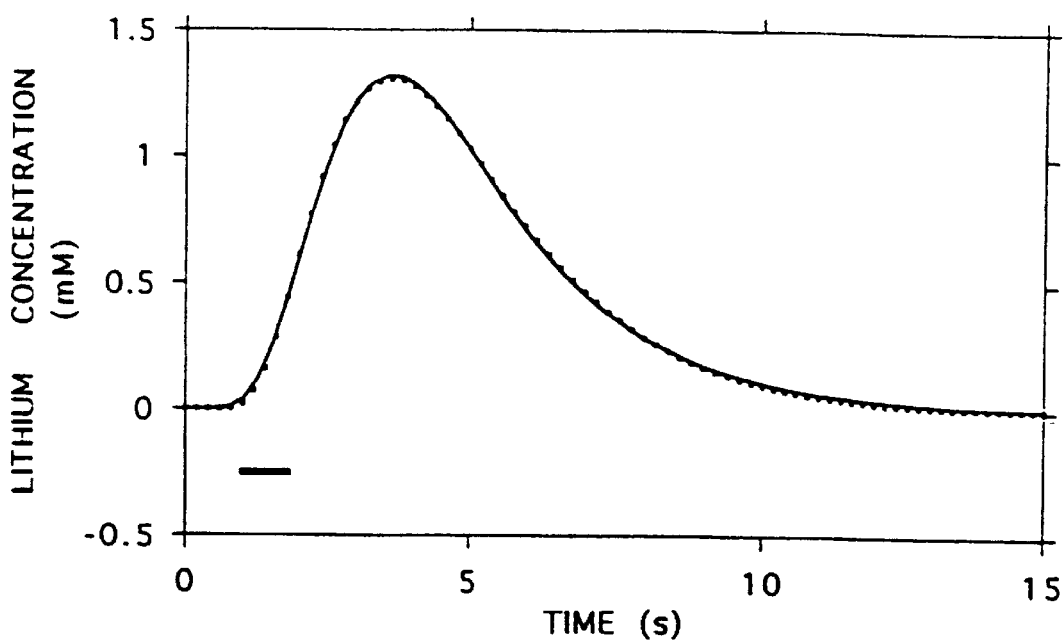
FIG. 3 illustrates the data points from the third curve of FIG. 2 (after the signal had passed through three filters) and the line illustrates the lognormal curve fitted by least squares regression. For the lognormal curve $\mu=1.53$, $\sigma=0.44$, and R=0.9998.
Figure 4:
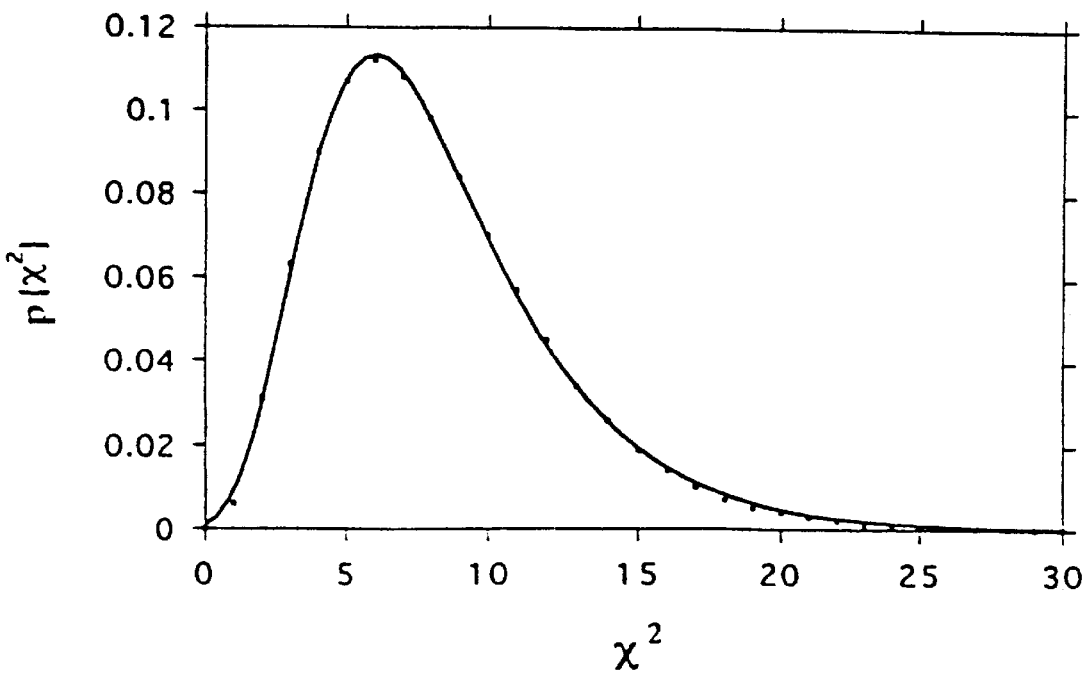
FIG. 4 illustrates the chi squared distribution (data points) for 8 degrees of freedom (equivalent to four filters) with a lognormal curve fitted using least squares regression. For the lognormal curve $\mu=2.32$, $\sigma=0.38$, and R=0.9997.
Figure 5:
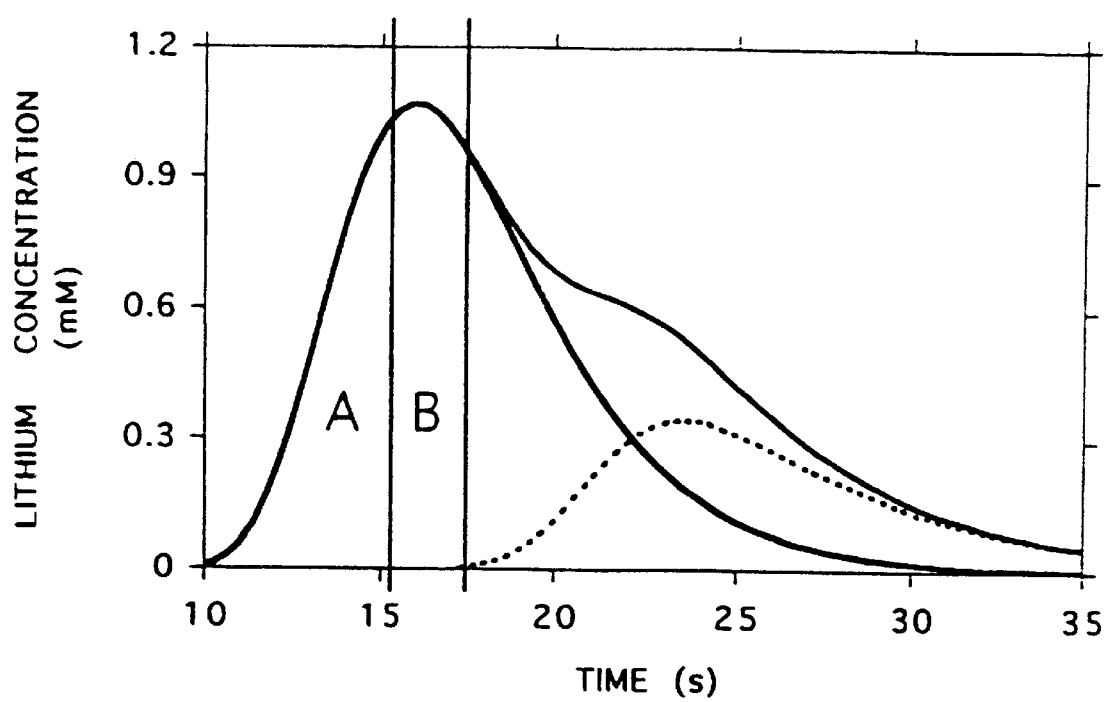
FIG. 5 illustrates an indicator dilution curve obtained from a model showing primary and secondary curves and the positioning of the first and second parts A and B to calculate the area under the primary curve.
Figure 6:
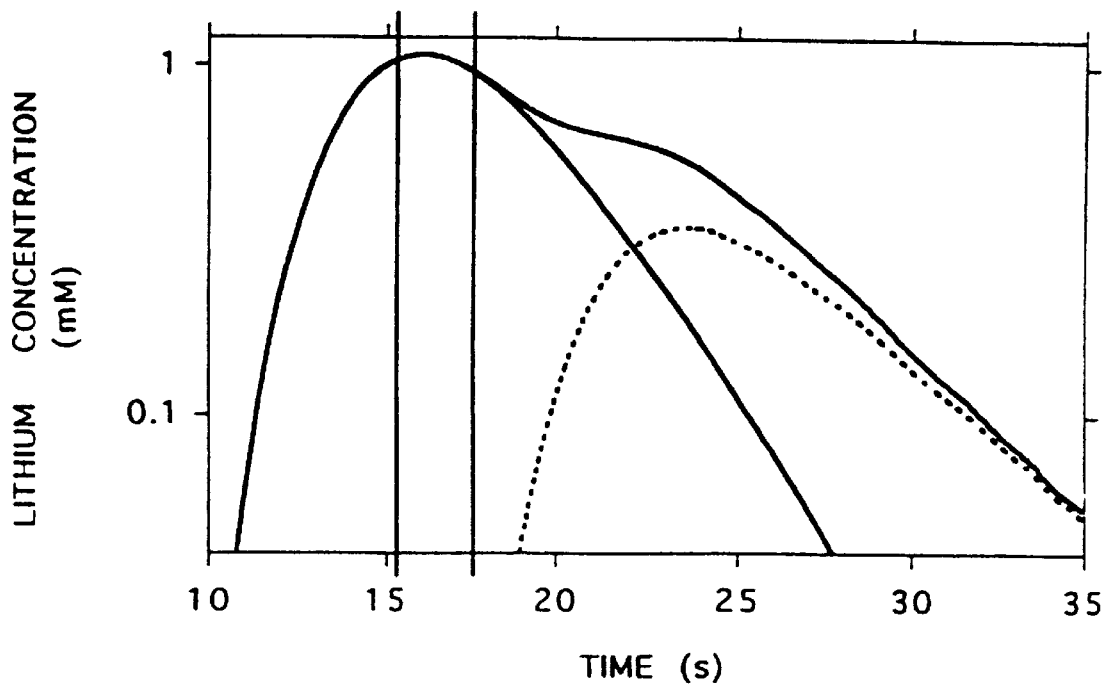
FIG. 6 is a semilogarithmic plot of the dilution curve of FIG. 5.

FIG. 5 illustrates an indicator dilution curve comprising primary and secondary curves. A first area A is defined as being the area under the curve (the integral) from the start of the curve to a predefined fraction of the peak height either before or after the peak. In the example shown in FIG. 5 the predefined fraction is 97% of the peak height up to the peak. A second area B is then defined from the edge of area A to a second predetermined fraction which in the example shown in FIG. 5 is a point 10% down the peak. The relationship between the total area under the primary lognormal curve and the areas under the first and second parts A and B is given by:

$$\frac{\text{Total area}}{A+B} = f\left(\frac{A}{B}\right)$$

-continued $$\text{Total area} = f\left(\frac{A}{B}\right) \times (A + B)$$

The relationship therefore depends on the function (f) and the two sides of the equation depend only on σ which is unique for each curve.

For a lognormal curve, at a fraction (F) of the peak height:

$$X_F = e^{\left\{\mu - \sigma^2 \pm \sigma \sqrt{2\ln(F^{-1})}\right\}}$$

(± depending on whether F is before (−) or after (+) the peak)

$$\text{Area up to } F = \alpha \times \phi\left\{\frac{\ln(X_F) - \mu}{\sigma}\right\}$$
$$= \alpha \times \phi\left\{-\sigma \pm \sqrt{2\ln(F^{-1})}\right\}$$

where α=total area
and φ is the cumulative normal distribution function.

$$\phi(X) = \frac{1}{\sqrt{2\pi}} \int_{-\alpha}^{X} e^{-0.5t^2} dt$$

Thus $$A = \alpha \times \phi\left\{-\sigma \pm \sqrt{2\ln(F_A)}\right\}$$
$$B = \alpha \times \phi\left\{-\sigma \pm \sqrt{2\ln(F_B)}\right\}$$

where $F_A$ and $F_B$ are the fractions of the peak delineating A and B.

In FIG. 5 a first portion of the curve from the beginning to a point beyond the peak, but short of where recirculation starts, is divided into two roughly equal areas A and B. Preferably these areas are roughly equal to ensure that the ratio A/B is not over-sensitive to errors in A or B. The more of the curve which is used, the greater the accuracy of the determination of the area. The area available for integration is however restricted by the extent to which the secondary curve caused by recirculation overlaps the primary curve. It is also best to avoid using the peak as the line separating A and B, since if this is rather "rounded" a small error in the Y co-ordinate will lead to a large error in X and hence in the estimations of A and B. Therefore, the fraction 1 (or 100%) for delineating A and B should be avoided.

In FIG. 5 area A is the area up to 97% of the peak whereas area B is the area as far as 90% of the peak on the descending limb minus the area up to 97% of the peak (A). Thus $$A = \alpha \times \phi\left\{-\sigma - \sqrt{2\ln(0.97^{-1})}\right\}$$
$$B = \alpha \times \phi\left\{-\sigma + \sqrt{2\ln(0.9^{-1})}\right\}$$

Figure 7:
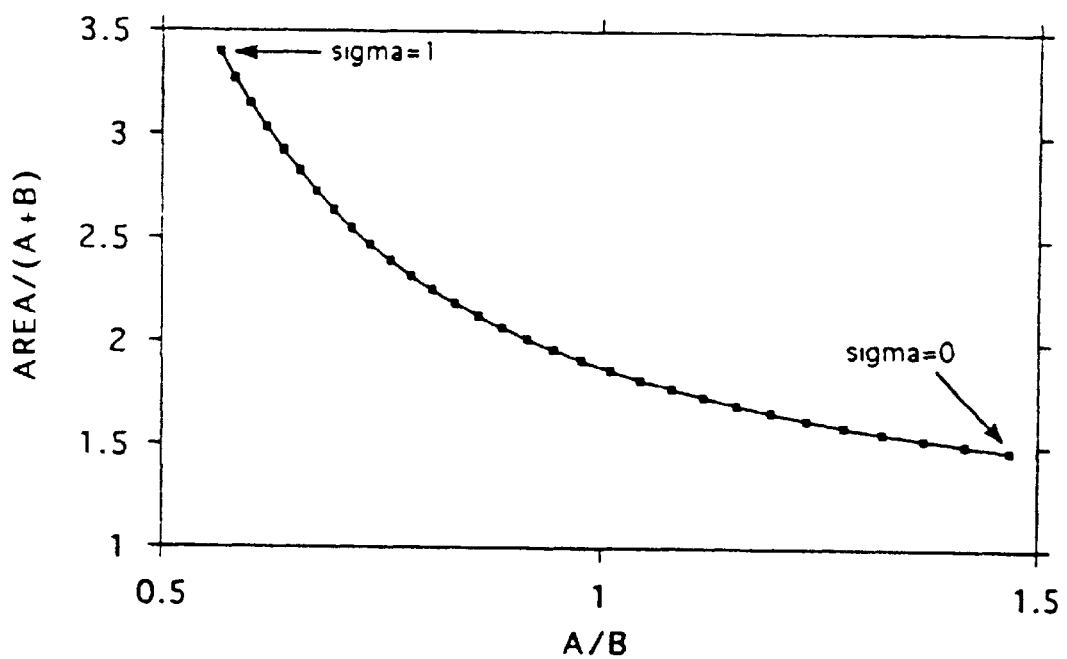
FIG. 7 is a plot of the total area divided by (A+B) plotted against the corresponding values of A/B for $\sigma=0$ to 1 and for area A delineated up to 97% of the peak and area B being delineated to 10% down from the peak minus A (as illustrated in FIG. 5).

Using these equations the ratios A/B and α/A+B can be found for different values of σ using normal distribution tables. FIG. 7 shows the values of α/A+B plotted against corresponding values of A/B for σ values of 0 to 1 (which is the range of skewness normally found in indicator dilution curves and is also the range of skewness for which the chi squared distribution can be reasonably approximated by a lognormal distribution). The line joining the points was derived using an iterative programme to derive an equation for the curve which is given by $$\alpha/(A+B) = 1.2401 + 44.0371 \times e^{(-7.3741 \times A/B)} - 4.6350 \times e^{(-2.0271 \times A/B)}$$

Thus $$\alpha = \{1.2401 + 44.0371 \times e^{(-7.3741 \times A/B)} + 4.6350 \times e^{(-2.0271 \times A/B)}\} \times (A+B)$$

Thus for σ in the range 0 to 1 the integral of the complete lognormal curve can be derived merely from the integral of the first and second parts of the lognormal curve A and B.

FIG. 7 illustrates the plot of α/A+B against A/B for the specific selected fractions for A and B shown in FIG. 5. The curve will be different for any other selected fractions. Thus, in order to enable the integral of a complete lognormal distribution to be determined, the equation defining the relationship between α/(A+B) and A/B for specific fractions must be determined to enable the equation to be used in the calculation of the integral of the complete lognormal distribution. Alternatively, values for α for a range of ratios of A and B and a range of fractions $F_A$ and $F_B$ can be stored in a look-up table. The determination of α can then simply be carried out by looking up the value of α for the selected fractions $F_A$ and $F_B$ and for the calculated ratio A/B.

Figure 8:
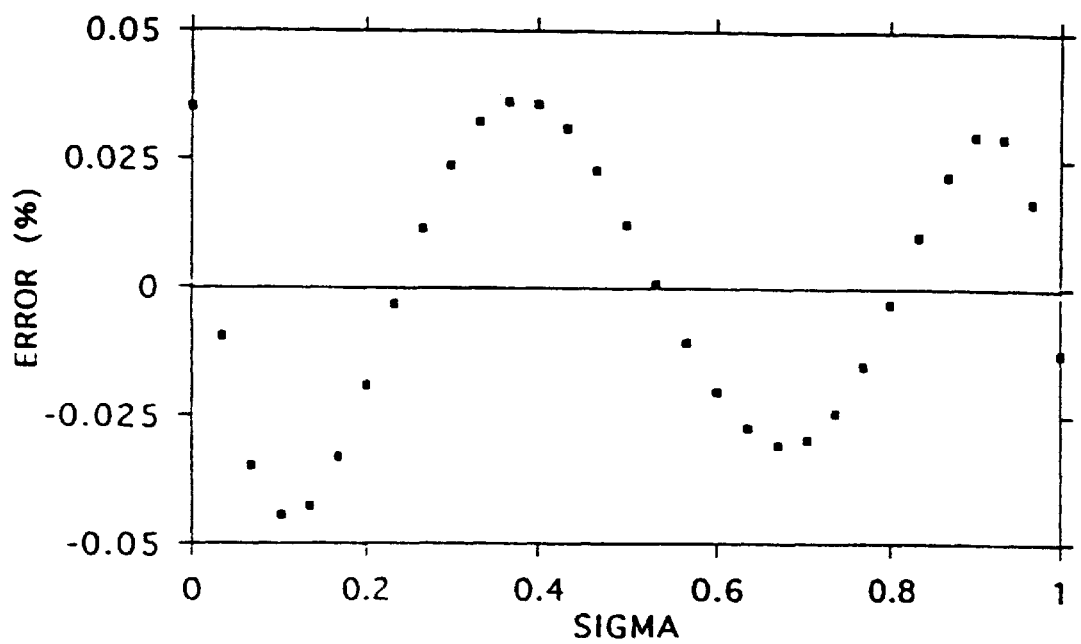
FIG. 8 illustrates the percentage error in deriving the area under the lognormal curves using the equation of the line from the data illustrated in FIG. 7.

This technique for determining the integral of the complete lognormal distribution from the integrals of only two parts of the lognormal distribution in a first portion of the lognormal distribution is quite accurate as can be seen in FIG. 8. The error is less than ±0.05% for a range of σ from 0 to 1.0.

Thus using the equations given herein above it is possible to determine cardiac output from an indicator dilution curve merely by determining the integral of two parts of a first portion of the lognormal distribution. This not only avoids the necessity to measure the concentration for a significantly longer time (thus making the measurement time shorter and reducing any trauma to a patient) but also the technique avoids the problem of recirculation.

Although this technique is particularly applicable to the analysis of indicator dilution curves, it is applicable to the analysis of any signals which represent a physical parameter exhibiting a skew distribution. The signal can exhibit a temporal or spatial skew distribution. The technique of the present invention can be used where the integral over the complete skew distribution is required but cannot be obtained directly either because the complete distribution cannot be measured or because of interference in the latter part of the distribution.

The technique of the present invention advantageously uses the early part of the curve to predict the tail. This is in contrast to the Hamilton method which uses the rather short part of the decay before recirculation occurs to predict the tail.

Since the technique of the present invention uses the integration of the area under the curve, the smoothing of the curve by the use of a filtering technique does not affect the area nor the lognormal characteristic and thus can be used to filter out noise and provide for a more accurate delineation of the first and second areas.

The technique of the present invention is also advantageous over prior art techniques since where the distribution is a temporal distribution the time taken to take the necessary measurement to be able to determine the integral of the complete skew distribution is reduced. Thus for indicator dilution curves, the time for which blood is sampled past the sensor can be reduced since less of the curve is required.

The technique of the present invention is further advantageous in that it is more accurate because even when there is enough of the primary curve to allow the monoexponential extrapolation technique of Hamilton, this technique still provides an over-estimate of the lognormal integral.

A further advantage of the present invention is that the technique is computationally efficient. The present invention is preferably carried out by digitizing the signal representing the physical parameter, e.g. from a sensor, integrating the first and second parts of the signal, and carrying out the calculations given in the equations hereinabove by suitable programming. The computational steps required to implement the equations hereinabove are small compared with the computational steps required in the techniques of the prior art.

Apparatus for carrying out the present invention can comprise any suitably programmed compute such as an IBM compatible computer or a Macintosh personal computer. For the analysis of indicator dilution curves, the apparatus for measuring cardiac output will include a blood sensor such as that disclosed in WO93/09427. The output of the sensor must then be digitized by an analogue-to-digital converter and input into the computer. For any other form of signals representing physical parameters, similarly, the output of some sort of transducer must be digitized to provide digital signals for analysis by the software loaded in a computer.

The software loaded in the computer will then carry out all of the steps of analysis to determine the integral of the complete skew distribution. Preferably the filtering of the signals to remove noise is carried out digitally although the signal can be analoguely filtered prior to being digitized and input into the computer.

The computer program running on the computer can either display the result of the integration or can output this to some other device. Where the data indicates flow, e.g. an indication dilution curve, the result of the integration will be the flow rate or cardiac output which can be displayed on a computer display screen or output to a device such as a printer.

In order to determine the predetermined relationship between the integral of the total skew distribution and the integrals of the first and second parts of the skew distribution, a commercially available iterative curve fitting program such as a KaleidaGraph (trade mark) can be used.

What is claimed is:

1. A method of analyzing a signal representing a physical parameter for at least one of the purposes: (i) to obtain information from said signal, (ii) to extrapolate information contained in said signal and (iii) to ignore an interfering component in part of said signal, said signal representing one of the group consisting of only a first portion of a skew distribution, and a first portion of a skew distribution, and a second portion containing said interfering component, said method comprising the steps of:
   a) selecting two fractions of the maximum value of said signal in said first portion and selecting whether said fractions are to represent positions on said skew distribution having a positive or negative slope, said fractions being used to delineate between first and second parts of said skew distribution, said first and second parts being delineated to lie within said first portion of said skew distribution,
   b) determining the integrals of said first and second parts, and
   c) determining the integrals of said complete skew distribution using said determined integrals of said first and second parts and a predetermined relationship between the integral of a complete skew distribution and functions of integrals of said first and second parts for said selected fractions.

2. A method as claimed in claim 1 wherein said skew distribution is a chi squared distribution.

3. A method as claimed in claim 1 wherein said skew distribution can be approximated as a lognormal distribution.

4. A method as claimed in claim 1 including the step of filtering said signal to remove noise before the step of determining the integrals of said first and second parts.

5. A method as claimed in claim 1 wherein said fractions are selected such that the integrals of said first and second parts are substantially equal.

6. A method as claimed in claim 1 wherein said fractions are less than 1.

7. A method as claimed in claim 1 wherein said signal represents a temporal skew distribution for said physical parameter, said step of determining the integral of said complete skew distribution providing a measure of the quantum of said physical parameter.

8. A method as claimed in claim 1 wherein said signal represents the concentration of a substance in a flowing fluid, and said determined integral of said complete skew distribution being used to calculate the flow rate of said fluid.

9. A method as claimed in claim 1 wherein said signal represents current and said determined integral of said complete skew distribution represents charge.

10. A method as claimed in claim 1 wherein said relationship is determined by equating said integral of said complete skew distribution divided by the sum of the integral of said first part and the integral of said second part with a function of the ratio of the integral of said first part to the integral of said second part.

11. A method as claimed in claim 1 wherein said skew distribution is approximated as a lognormal distribution and said relationship is determined from the equations $$A = \alpha \times \phi\left\{-\sigma \pm \sqrt{2\ln(F_A^{-1})}\right\}$$

$$B = \alpha \times \phi\left\{-\sigma \pm \sqrt{2\ln(F_B^{-1})}\right\}$$

and $$\phi(x) = \frac{1}{\sqrt{2\pi}} \int_{-\alpha}^{X} e^{-0.5t^2} dt$$

where
   A is the integral of said first part
   B is the integral of said second part
   $\alpha$ is the integral of said complete skew distribution
   $\sigma$ is the standard deviation of the normal distribution from which the logarithmic transformation was obtained and which indicates the degree to which said distribution is skew
   $F_A$ is a first of said preselected fractions delineating said first and second parts
   $F_B$ is a second of said preselected fractions delineating said second part and any further part of said skew distribution
   $\phi$ is the cumulative normal distribution function
   t is time
   x is the signal value, and
   ± determines whether said preselected fractions $F_A$ and $F_B$ are on a positive slope (−) or on a negative slope (+).

12. A method as claimed in claim 1 wherein values for the integral of complete skew distributions for different ratios of the integral of said first and second parts, for different fractions selected in said selecting step, and for different degrees of skewness are prestored in a look-up table, said step of determining the integral of said complete skew distribution comprising the step of calculating the ratio of the integral of said first and second parts, and looking-up the integral of said complete skew distribution using said selected fractions and the ratio calculated in said calculating steep.

13. A method as claimed in claim 1 wherein said signal represents a spatial skew distribution for said physical parameter, said step of calculating the integral of said complete skew distribution providing a measure of the quantum of the spatially distributed said physical parameter.

14. A method of measuring flow rate of a fluid comprising the steps of
   a) adding a known quantity of a substance into said fluid at a point in time,
   b) measuring the quantity of said substance in said fluid at a point downstream to generate a signal, and
   c) analyzing said signal in accordance with the method of claim 1.

15. A method as claimed in claim 14 wherein said substance is soluble in said fluid and the concentration of said substance in said fluid is measured at said downstream point.

16. A method of determining the flow rate of a fluid comprising the steps of:
   a) adding a known quantity of a substance to said fluid at a point in time,
   b) measuring the quantity of said substance in said fluid at a point downstream to generate a distribution with respect to time, said distribution approximating either only a first portion of a skew distribution, or a first portion of a skew distribution and a second portion containing extraneous components,
   c) assuming said distribution can be approximated by a skew distribution and selecting two fractions of the maximum value of said signal in said first portion and selecting whether said fractions are to represent positions on said skew distribution having a positive or a negative slope, said fractions being used to delineate between first and second parts of said skew distribution, said first and second parts being delineated to lie within said first portion of said skew distribution,
   d) calculating the integrals of said first and second parts,
   e) determining the integral of the complete skew distribution using said calculated integrals of said first and second parts and a predetermined relationship between functions of the integrals of said first and second parts and the integral of said complete skew distribution for said selected fractions, and
   f) calculating the flow rate of said fluid from said known quantity of said substance and said integral of said complete skew distribution.

17. A method as claimed in claim 16 including the step of digitizing the measurement of the quantity of said substance, and storing said digitized measurement for analysis.

18. A method as claimed in claim 16 wherein said step of calculating the flow rate comprises the step of dividing the determined integral of said complete skew distribution into said known quantity of said substance.

19. A method as claimed in claim 16 wherein said skew distribution can be approximated to a lognormal distribution.

20. A method as claimed in claim 16 including one of the steps from the group consisting of filtering and integrating said distribution to remove noise before the step of calculating the integral of said first and second parts.

21. A method as claimed in claim 16 wherein said fractions are selected such that the integrals of said first and second parts are substantially equal.

22. A method as claimed in claim 16 wherein said fractions are less than 1.

23. A method as claimed in claim 16 wherein said relationship is determined by equating said integral of said complete skew distribution divided by the sum of the integral of said first part and the integral of said second part with a function of the ratio of the integral of said first part to the integral of said second part.

24. A method as claimed in claim 16 wherein said skew distribution is approximated as a lognormal distribution and said relationship is determined from the equations $$A = \alpha \times \phi\left\{-\sigma \pm \sqrt{2\ln(F_A^{-1})}\right\}$$

$$B = \alpha \times \phi\left\{-\sigma \pm \sqrt{2\ln(F_B^{-1})}\right\}$$

and $$\phi(X) = \frac{1}{\sqrt{2\pi}} \int_{-\alpha}^{X} e^{-0.5t^2} dt$$

where
   A is the integral of said first part
   B is the integral of said second part
   $\alpha$ is the integral of said complete skew distribution
   $\sigma$ is the standard deviation of the normal distribution from which the logarithmic transformation was obtained and which indicates the degree to which said distribution is skew
   $F_A$ is a first of said preselected fractions delineating said first and second parts
   $F_B$ is a second of said preselected fractions delineating said second part and any further part of said skew distribution
   $\phi$ is the cumulative normal distribution function
   t is time
   x is the signal value, and
   $\pm$ determines whether said preselected fractions $F_A$ and $F_B$ are on a positive slope (−) or on a negative slope (+).

25. A method as claimed in claim 16 wherein values for the integrals of complete skew distributions for different ratios of the integrals of said first and second parts, for different said selected fractions, and for different degrees of skewness are prestored in a look-up table, said step of determining the integral of said complete skew distribution comprising the step of calculating the ratio of the integrals of said first and second parts, and looking-up the integral of said complete skew distribution using said selected fractions and said calculated ratio.

26. Apparatus for analyzing a signal representing a physical parameter for at least one of the purposes: (i) to obtain information from said signal, (ii) to extrapolate information contained in said signal and (iii) to ignore an interfering component in part of said signal, said signal representing one of a group consisting of only a first portion of a skew distribution and a first portion of a skew distribution, and a second portion containing said interfering component, said system comprising:
   a) means for selecting two fractions of the maximum value of said signal in said first portion and selecting whether said fractions are to represent positions on said skew distribution having a positive or a negative slope, said fractions being used to delineate between first and second parts of said skew distribution, said first and second parts being delineated to lie within said first portion of said skew distribution, b) means for determining the integrals of said first and second parts, and c) means for determining the integrals of said complete skew distribution using said determined integrals of said first and second parts and a predetermined relationship between the integral of a complete skew distribution and functions of integrals of said first and second parts for said selected fractions.

27. Apparatus as claimed in claim 26 wherein said means for determining the integral of said complete skew distribution uses a relationship between the integral of a complete lognormal distribution and integrals of said first and second parts for said selected fractions.

28. Apparatus as claimed in claim 26 including filter means for filtering said signal to remove noise before the integrals of said first and second parts are determined.

29. Apparatus as claimed in claim 26 including means to determine said relationship by equating said integral of said complete skew distribution divided by the sum of the integral of said first part and the integral of said second part with a function of the ratio of the integral of said first part to the integral of said second part.

30. Apparatus as claimed in claim 26 wherein said skew distribution is approximated as a lognormal distribution including means to determine said relationship using the equations:

$$A = \alpha \times \phi\left\{-\sigma \pm \sqrt{2\ln(F_A^{-1})}\right\}$$

$$B = \alpha \times \phi\left\{-\sigma \pm \sqrt{2\ln(F_B^{-1})}\right\}$$

and $$\phi(X) = \frac{1}{\sqrt{2\pi}} \int_{-\alpha}^{X} e^{-0.5t^2} dt$$

where

A is the integral of said first part

B is the integral of said second part $\alpha$ is the integral of said complete skew distribution $\sigma$ is the standard deviation of the normal distribution from which the logarithmic transformation was obtained and which indicates the degree to which said distribution is skew $F_A$ is a first of said preselected fractions delineating said first and second parts $F_B$ is a second of said preselected fractions delineating said second part and any further part of said skew distribution $\phi$ is the cumulative normal distribution function t is time x is the signal value, and $\pm$determines whether said preselected fractions $F_A$ and $F_B$ are on a positive slope (−) or on a negative slope (+).

31. Apparatus as claimed in claim 26 including a look-up table containing values for the integrals of complete skew distributions for different ratios of the integrals of said first and second parts, for different said selected fractions, and for different degrees of skewness, said means for determining the integral of said complete distribution comprising means for calculating the ratios of the integrals of said first and second parts, and means for looking-up the integral of said complete skew distribution using said selected fractions and said calculated ratio.

32. Apparatus for determining the flow rate of a fluid comprising:

a) sensor means for measuring the quantity of a substance in said fluid at a point downstream of where a known quantity said substance has been added to said fluid, the measurement generating a distribution with respect to time which approximates either only a first portion of a skew distribution, or a first portion of a skew distribution and a second portion containing extraneous components, b) means for selecting two fractions of the maximum value of said signal in said first portion and selecting whether said fractions are to represent positions on said skew distribution having a positive or a negative slope, said fractions being used to delineate between first and second parts of said skew distribution, said first and second parts being delineated to lie within said first portion of said skew distribution, c) means for calculating the integrals of said first and second parts, d) means for determining the integral of the complete skew distribution using said calculated integrals of said first and second parts and a predetermined relationship between functions of integrals of said first and second parts and the integral of said complete skew distribution for said selected fractions, and e) means for calculating the flow rate of said fluid from said known quantity of said substance and said integral of said complete skew distribution.

33. Apparatus as claimed in claim 32 including digitizing means for digitizing said measurement, and storage means for storing the digitized measurement for analysis.

34. Apparatus as claimed in claim 32 wherein said means for calculating the flow rate comprises means for dividing the determined integral of said complete skew distribution into said known quantity of said substance.

35. Apparatus as claimed in claim 32 including filter means to filter said measurement to remove noise before calculating the integrals of said first and second parts.

36. Apparatus as claimed in claim 32 including means for predetermining the relationship by equating said integral of said complete skew distribution divided by the sum of the integral of said first part and the integral of said second part with a function of the ratio of the integral of said first part to the integral of said second part.

37. Apparatus as claimed in claim 32 including means for predetermining the relationship by assuming said skew distribution approximates a lognormal distribution and using the equations:

$$A = \alpha \times \phi\left\{-\sigma \pm \sqrt{2\ln(F_A^{-1})}\right\}$$

$$B = \alpha \times \phi\left\{-\sigma \pm \sqrt{2\ln(F_B^{-1})}\right\}$$

and $$\phi(X) = \frac{1}{\sqrt{2\pi}} \int_{-\alpha}^{X} e^{-0.5t^2} dt$$

where

A is the integral of said first part

B is the integral of said second part $\alpha$ is the integral of said complete skew distribution $\sigma$ is the standard deviation of the normal distribution from which the logarithmic transformation was obtained and which indicates the degree to which said distribution is skew $F_A$ is a first of said preselected fractions delineating said first and second parts $F_B$ is a second of said preselected fractions delineating said second part and any further part of said skew distribution $\phi$ is the cumulative normal distribution function t is time x is the signal value, and ± determines whether said preselected fractions $F_A$ and $F_B$ are on a positive slope (−) or on a negative slope (+).

38. Apparatus as claimed in claim 32 including a look-up table containing values for the integrals of complete skew distributions for different ratios of the integrals of said first and second parts, for different said selected fractions, and for different degrees of skewness, said means for determining the integral of said complete distribution comprising means for calculating the ratios of the integrals of said first and second parts, and means for looking-up the integral of said complete skew distribution using said selected fractions and said calculated ratio.

* * * * *

UNITED STATES PATENT AND TRADEMARK OFFICE
CERTIFICATE OF CORRECTION

PATENT NO. : 6,216,094 B1  
DATED : April 10, 2001  
INVENTOR(S) : Robert A.F. Linton et al.

Page 1 of 1

It is certified that error appears in the above-identified patent and that said Letters Patent is hereby corrected as shown below:

<u>Column 3,</u>  
Lines 17 and 18 (equation), please replace with the following equation:

$$\text{cardiac output in } \ell/\text{min} = \frac{\text{Indicator dose} \times 60}{\text{Total area} \times (1\text{-PCV})}$$

<u>Column 11,</u>  
Line 6, delete "steep" and insert -- step --.

Signed and Sealed this

First Day of January, 2002

Attest:

*Attesting Officer*

JAMES E. ROGAN  
*Director of the United States Patent and Trademark Office*